(12) United States Patent
Anup et al.

(10) Patent No.: US 10,189,055 B2
(45) Date of Patent: Jan. 29, 2019

(54) COLOR BASED OPTICAL GRADING SYSTEM WITH MULTI REFLECTANCE AND MULTI-ANGLE VIEWS

(71) Applicant: NANOPIX INTEGRATED SOFTWARE SOLUTIONS PRIVATE LIMITED, Hubli Dharwad, Karnataka (IN)

(72) Inventors: Vijapur Anup, Karnataka (IN); Krishnamoorthy Sasisekar, Karnataka (IN)

(73) Assignee: NANOPIX INTEGRATED SOFTWARE SOLUTIONS PRIVATE LIMITED, Hubli Dharwad, Karnataka (IN)

( * ) Notice: Subject to any disclaimer, the term of this patent is extended or adjusted under 35 U.S.C. 154(b) by 0 days.

(21) Appl. No.: 15/562,740

(22) PCT Filed: Mar. 31, 2016

(86) PCT No.: PCT/IN2016/000084
§ 371 (c)(1),
(2) Date: Sep. 28, 2017

(87) PCT Pub. No.: WO2016/157216
PCT Pub. Date: Oct. 6, 2016

(65) Prior Publication Data
US 2018/0071788 A1    Mar. 15, 2018

(30) Foreign Application Priority Data

Mar. 31, 2015 (IN) .......................... 1719/CHE/2015

(51) Int. Cl.
*G06T 7/90* (2017.01)
*B07C 5/342* (2006.01)
(Continued)

(52) U.S. Cl.
CPC ............ *B07C 5/342* (2013.01); *B07C 5/3425* (2013.01); *G01N 21/84* (2013.01); *G01N 21/88* (2013.01);
(Continued)

(58) Field of Classification Search
CPC ......... B07C 5/34; B07C 5/342; B07C 5/3425; G06T 7/90; G01N 21/84; G01N 21/88; G01N 21/892
(Continued)

(56) References Cited

U.S. PATENT DOCUMENTS 4,358,203 A * 11/1982 Citrin ..................... G01N 35/00
283/65
4,825,068 A * 4/1989 Suzuki ..................... B07C 5/10
250/223 R
(Continued)

FOREIGN PATENT DOCUMENTS

WO    WO-9732181 A1 * 9/1997 ........... B07C 5/3422

*Primary Examiner* — Terrell H Matthews
(74) *Attorney, Agent, or Firm* — Harness, Dickey & Pierce, P.L.C.

(57) ABSTRACT

The present invention discloses a novel color based optical grading system with multi-reflectance and multi-angle views for grading objects of different external characteristics, and a novel color based optical grading method for grading objects based on different external characteristics. The system comprises of: multiple advanced optics units and at least one master controller. Each optics unit comprises of multiple programmable cameras, multiple spectral light sources, multiple adjustable mirrors/prisms, a mirror/prism adjustment assembly to ensure the enhanced surface analysis of the objects; at least one backlighting domes to provide uniform backlight for capturing objects in multi-reflection and multi-angle views and at least one image processing unit for processing images of each objects. The system is capable of not only identifying the type or color grade of individual
(Continued)

object with enhanced accuracy, but is also efficient in analyzing different objects based on external characteristics like different sized objects are analyzed due to functioning of multiple adjustable mirrors or prisms. The system is automated and accurate color grading system which is capable of not only analyzing all possible color variations of any object, but is also capable of analyzing all other possible external characteristics.

10 Claims, 4 Drawing Sheets

(51) Int. Cl.
  *G01N 21/84* (2006.01)
  *G01N 21/88* (2006.01)
  *G01N 21/892* (2006.01)
(52) U.S. Cl.
  CPC .......... *G01N 21/892* (2013.01); *G06T 7/90* (2017.01); *B07C 2501/00* (2013.01); *B07C 2501/009* (2013.01); *B07C 2501/0081* (2013.01); *G01N 2021/845* (2013.01)

(58) Field of Classification Search
  USPC .......................................................... 209/580
  See application file for complete search history.

(56) References Cited

U.S. PATENT DOCUMENTS

| | | | | |
|---|---|---|---|---|
| 5,845,002 | A * | 12/1998 | Heck ................... | B07C 5/3416 382/110 |
| 5,917,926 | A * | 6/1999 | Leverett ............... | B07C 5/3422 209/585 |
| 8,928,023 | B1 | 1/2015 | Coleiny et al. | |
| 8,988,523 | B1 | 3/2015 | Kim et al. | |
| 2002/0014533 | A1* | 2/2002 | Zhu ...................... | B82Y 15/00 235/472.01 |
| 2006/0132759 | A1* | 6/2006 | Jeong ............... | G01N 21/95684 356/237.4 |
| 2006/0151604 | A1* | 7/2006 | Zhu ...................... | G06K 7/14 235/454 |
| 2012/0312104 | A1* | 12/2012 | Hamamatsu ....... | G01N 21/8851 73/865.8 |
| 2015/0177157 | A1* | 6/2015 | Edmondson ......... | G01N 33/025 348/125 |

\* cited by examiner

COLOR BASED OPTICAL GRADING SYSTEM WITH MULTI REFLECTANCE AND MULTI-ANGLE VIEWS

FIELD OF THE INVENTION

The present invention relates generally, to optical grading systems and methods for grading objects and, in particular, relates to a novel color based optical grading system for grading objects of different external characteristics and a novel color based optical grading method for grading objects.

BACKGROUND OF THE INVENTION

In our day to day life, we come across a common necessity of selecting any object from a group of given quantity of objects of various colors or representative colors or shades. Objects which conform to certain grading, it is highly desirable to grade any object where color of the object is of higher commercial value. Color grading is used widely to characterize various naturally occurring objects or artificially produced objects like precious stones, gems etc.

Objects having naturally-occurring color variations can be different agricultural products such as grains, different nuts, fruits, vegetables etc. or artificially produced objects such as processed food products and are graded according to their colors, length, cut size, and defect data, etc. are graded which is a very well known process using some sorting or grading machine. Generally, the objects to be graded are kept on the moving conveyor and past an optical grading system or inspection system where they are automatically graded or sorted and then collected according to some desired characteristic of the produce and these desired characteristics are most commonly, the color variation of objects along with other external characteristics. For color grading/sorting of different objects, this optical grading system is associated with color and intensity of light reflected from a single object based according to color and intensity variation. Therefore, the optical grading system should be capable to identify, inspect color variations significantly. With moving conveyor on which objects to be graded are placed are conveyed with high speed or variations in speed, variations in type of object to be graded based on size, shape, color, surface characteristics, the vibration and sometimes rolling of objects on the conveyor will cause variations in the viewing distance and viewing angle when the objects pass through the optical grading system, due to which there is great difficulty in producing consistent signals which leads to poor color grading and such poorly graded objects stand commercially less valuable due to the inefficiency of the current color grading systems to view the objects in detail to detect color variations, surface defects/damages etc. To overcome these shortcomings, few inventions have been developed to provide different optical grading systems. Incidentally, Patent Document 1 (U.S. Pat. No. 4,979,815) titled "Laser range imaging system based on projective geometry" discloses an apparatus and a method for producing a range image of an area of the surface of an object, by viewing illuminated light beam on the surface of the object. Here, by projecting a substantially planar beam of light onto the surface to illuminate the surface along a light stripe. The illuminated light beam is viewed and converted into an image generating the range image of the object. A three dimensional (3D) image of the object is formed by moving the object while it is scanned. By measuring only the top view and the profile view the volume estimation may also be inaccurate, especially when the objects have a very irregular shape. By using a planar beam of light situated above the moving object only the visible part of the object facing the capturing means can be detected, from which a two dimensional image will be formed. Parts of the object such as parts of the surface that is not in line of sight from the viewpoint of the capturing means as well as all the downwardly facing parts of the object will not be visible for the capturing means as will therefore appear as blanks in the captured image. This causes an increase in uncertainty in the measurement, and therefore the apparatus and the related method fails to provide accurate color grading. Patent Document 2 (U.S. Pat. No. 5,184,733) titled "Apparatus and method for determining the volume, form and weight of objects" which includes a line scan camera to record a top view of the object and simultaneously to record a profile view of the object through a mirror positioned on a fixed support at the side of a conveyor. From these data the width and the height of the object is determined. Accordingly, the composition image of the object consists of many cross-sections, with the width and the maximum thickness of the object being measured in each cross-section. By determining only the width and height of the object, the errors can be very high, especially when the object has irregular structure which leads to inefficient color grading of objects. In both Patent Document 1 and 2, the accuracy of the image getting from side views is not sufficient enough for effective color grading of objects.

Patent Document 3 (Chinese Patent Pub. No. CN103056111) titled "Prawns quality detecting and classifying device based on machine vision technology", discloses a machine vision technology which includes a single camera fixed at the top end of a lighting box above the conveyor belt, and a white unsmooth coating is painted on inner walls of the lighting box. Light source illuminates upwards, and reflects to the surface of the prawn through the white coating of the inner walls so capturing only top views of object. A single camera and a light source to capture only one side of object fail to provide an accurate grade of object. For efficient color grading, object must be viewed clearly from all the sides to know even a smaller color defect.

Patent document 4 is our previously filed Patent application (WIPO Publication No. WO2015128872), titled "An improved machine for grading small sized irregular objects and a process thereof" discloses a grading machine comprising with imaging systems with multi-wavelength lighting system for surface property extraction of any small sized, irregular or uneven object of interest and also having multi-vision transparent tray assembly with transparent cups to accommodate one object in one cup. These imaging systems are programmed in such a way that they can see multiple sides of the single given object of a single cup, to decide the category of that object, but the disclosed grading machine lacks in deciding views and multi-reflectance due to lack of due to lack of mirrors/prisms or multiple programmable cameras for each object individually, therefore it suggests further tremendous scope in development of technology. Due to complexity involved in capturing multi-reflectance and multi-angle views of objects, even after using multiple cameras to view the object three dimensionally the current systems are unable to grade the objects of interest efficiently according to different external characteristics including size, shape, color variations, surface characteristics like surface defects/damages such as water marks, oil marks, surface properties or any other characteristics.

Accordingly, for further advancements in the existing optical grading system which is simple, easy to install in any grading system, and which deals with accurate, color grading of large range of objects with multi-reflection and multi-angle view based analysis of objects to effectively grade objects according to different external characteristics. Therefore, it would be highly desirable to provide a novel color based optical grading system with multi-reflectance and multi-angle views for grading accurately different types of objects in multiple grades in a single pass, which is simple, portable, and easy to install in any grading machine and also to provide a novel color based optical grading method for grading different types of objects rapidly and accurately into multiple grades in a single pass to increase the efficiency of any grading machine, thereby obviating all abovementioned shortcomings of the existing optical grading systems.

SUMMARY OF THE INVENTION

The present invention has been devised in the light of above mentioned existing circumstances of shortcomings of existing optical grading systems and related methods to overcome existing said shortcomings by providing a novel color based optical grading system with multi-reflectance and multi-angle views for grading objects and a novel color based optical grading method for grading objects.

The present invention mainly focuses on cashew nuts, but not limited to cashew kernel wherein the shape of cashew is curved at sides and can have many variations in their color surface properties. Since cashew nuts are curved in shape, the husk sometimes remains attached to the side part of the cashew nuts and cannot be detected generally with current optical inspection technologies. It affects quality of export of cashew nuts because of the export norms around 5% or more cashew nuts with husk are considered as rejected. Therefore, it is extremely crucial to analyze multi-reflection and multi-angle based views of cashew nuts and other any regular or irregular objects to get the accurate color grades to satisfy export quality norms.

The present invention provides a novel color based optical grading system with multi-reflectance and multi-angle views for grading objects. The novel color based optical grading system comprising of multiple advanced optics units which can be placed above and below the transparent conveyor of any grading machine for detailed analysis of each object and the functioning of each advanced optics unit of the entire optical grading system is controlled by the master controller for accurate analysis of each object with multi-reflectance and multi-angle views for effective grading. Each advanced optics unit comprises multiple programmable cameras, multiple-spectral light sources, multiple mirrors/prisms, at least one mirror adjustment assembly, at least one backlighting dome and at least one image processing unit. Multiple-spectral light sources, multiple adjustable mirrors/prisms and a backlighting dome helps the multiple programmable cameras of each advanced optics unit analyze every detail of each object with multi-reflectance and multi-angle based views. The master controller receives data/signals from at least two advanced optics units for analyzing each object, wherein one advanced optics unit is placed below the conveyor and one advanced optics unit is placed above the conveyor. After receiving data/signals the master controller decides the final grade of each object by comparing the data obtained from two image processing units of two corresponding advanced optics units according to the priority of color defects. Therefore, the present invention is most suitable to analyze each smaller detail of each object from multiple sides to get the exact grade of each object as it is an important task for any industry not limited to cashew nut industry. Accordingly, few objects of the present invention are listed below:

The main object of the present invention is to provide a simple, accurate and novel to a novel color based optical grading system with multi-reflectance and multi-angle views for grading regular, irregular, uneven, homogenous, non-homogenous or dissimilar or alike objects into multiple grades in a single pass based mainly on external characteristics like size, shape, color, defects, water marks, oil marks, surface properties or any other characteristics by using an advanced optics unit. Multiple programmable cameras of one advanced optics unit work collaboratively to send data to its image processing unit for multi-reflection and multi-angle view based analysis of each object. The advanced optics unit enhances the sideways features of the objects like sideways lighting from different sides using multiple reflections from multiple angles, so that multiple programmable cameras in each optics unit can analyze objects from all side views and also from top and bottom views for accurate complete analysis of each object.

It is another object of the present invention to provide a novel color based optical grading system which is automated for accurate color grading and is capable of not only analyzing all possible color variations of any object, but is also capable of analyzing all other possible external characteristics.

It is still another object of the present invention to provide a novel color based optical grading system which is programmed and automated for increased efficiency.

It is further object of the present invention to provide a novel color based optical grading system which is capable of identifying the type or color grade of individual object with enhanced accuracy in each advanced optics unit due to collaborative functioning of multiple programmable cameras, multiple spectral light sources, multiple adjustable mirrors/prisms, and a backlighting dome due to multi-reflection and multi-angle based views of each object for accurate grading, wherein the disclosed novel optical grading system is applicable for different sized objects due to functioning of multiple adjustable mirrors or prisms.

It is still further object of the present invention to provide a novel color based optical grading system which comprises of at least one master controller for single said optical grading system to receive data/signals from at least two advanced optics units for analyzing accurately each object.

It is another object of the present invention to provide a novel color based optical grading system which accepts objects to be graded through a specialized feeding unit for feeding objects singularly at pre-defined position on flat transparent surfaces of the conveyor of any grading machine into which the novel optical grading system is installed, so that single object occupies single flat transparent surface, wherein multiple flat transparent surfaces themselves make the conveyor which is in motion.

It is still another object of the present invention to provide a novel color based optical grading system for grading objects which enable in significantly improving the performance of any color based grading machine if installed therein, due to consideration of multi-reflection and multi-angle based views of each object for grading objects into multiple grades in a single pass, thereby ensuring a novel color based optical grading method to provide 'n' number of grades in a single pass which can be ejected as multiple grades in respective multiple collecting locations.

It is further object of the present invention to provide a novel color based optical grading method for grading different types of objects such as regular, irregular, uneven, homogenous, non-homogenous or dissimilar or alike objects into multiple color grades in a single pass with an enhanced accuracy and higher time efficiency.

It is still further object of the present invention to provide a novel color based optical grading system which is simple, portable, and easy to install in any grading machine for increasing efficiency of any grading machine having flat transparent surface of conveyor which is having multi-vision capacity.

The above mentioned and other objects, features, and advantages of the present invention will best be understood from the following description of various embodiments thereof, selected for the purposes of illustration, and shown in the accompanying drawings.

DETAILED DESCRIPTION OF THE INVENTION

Figure 1:
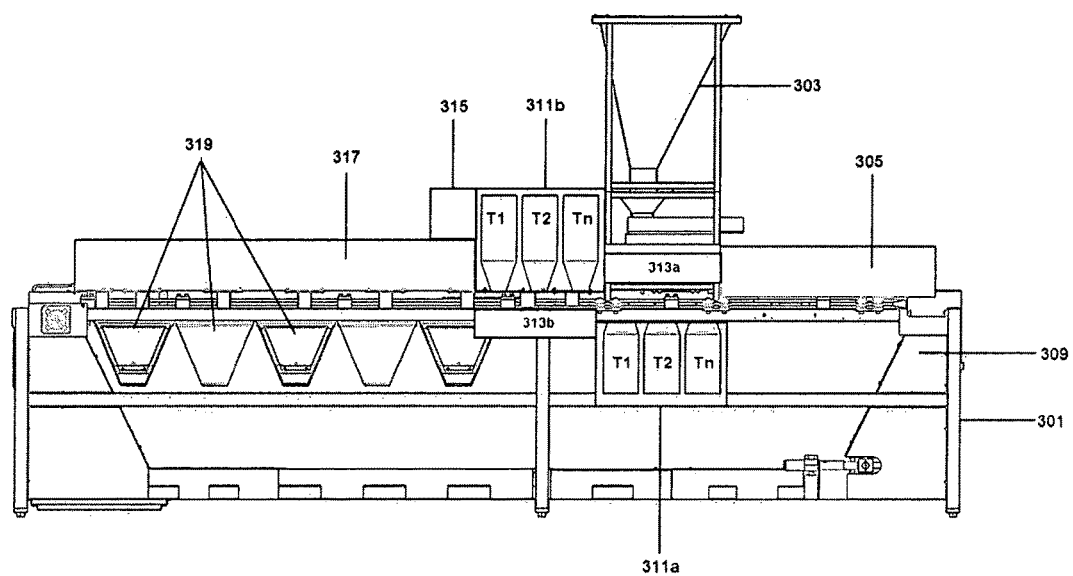
FIG. 1 is a schematic diagram illustrating an exemplary arrangement of non-limiting elements of a grading machine which is installed with a novel color based optical grading system of the present invention which works with a conveyor which is a transparent surface carrying objects to be graded according to one embodiment of the present invention.

The present invention will now be described with reference to the accompanying drawings. Now, refer in great detail to the exemplary drawings for the purposes of illustrating non-limiting embodiments of the present invention.

As used herein, the term 'object' shall refer to any regular, irregular, even, uneven, homogeneous, non-homogeneous material which includes any naturally occurring product including but not limited to any agricultural product like cashews, almonds, raisins, cloves, walnut, pistachios, or can be all culinary nuts, dry fruits, fruits, vegetable, grains, and other regularly or irregularly shaped objects like diced vegetables, processed food and the term 'object' also includes synthetically manufactured material including but not limited to plastic pellets, artificial stones, gems etc.

As used herein, the term 'irregular or uneven' shall refer to objects having differences in shape.

As used herein, the term 'external characteristics' shall refer to any external or extrinsic or morphological characteristics including, but not limited to size, shape, color variations, surface characteristics like surface defects/damages such as water marks, oil marks, surface properties or any other characteristics.

As used herein, the term 'homogeneous' shall refer to any one type of object like only almonds to be graded or only cashews to be graded or only artificial stones to be graded.

As used herein the term 'non-homogeneous' shall refer to mixture of different types of objects like a mixture of cashews and almonds or a mixture of plastic pellets and any one, two or more type of objects, wherein the term 'non-homogeneous' shall refer to any possible combination or variations of mixture of objects.

As used herein, the term 'novel optical grading system' comprises of multiple "advanced optics units" and at least one master controller, wherein each 'advanced optics unit' refers to a combination of multiple programmable cameras, multiple spectral light sources, multiple adjustable mirrors/multiple adjustable prisms, at least one backlighting dome and at least one mirror adjustment assembly and at least one "image processing unit" to ensure the enhanced surface analysis of the objects.

As used herein, the term 'transparent surface' refers to any transparent cup, or flat transparent cup, flat transparent surface with edges (bordered) or without edges, or any other possible variation of the transparent surface which is meant for multi-vision capacity for analysis of each object accurately.

As used herein, the term 'cameras' shall refer to the 'multiple programmable cameras' which are programmed as per the need of the invention and these cameras are multiple in number in each 'advanced optics unit'. These 'cameras' can be 'synchronous', 'asynchronous', 'regular', 'color' or 'multi-spectral', wherein the 'multi-spectral' cameras work at different frequencies of electromagnetic spectrum like visible, ultra-violet, infra-red etc.

As used herein, the term 'master controller' refers to a programmable controlling means which stores pre-determined data related to different external characteristics of different objects and decides accurate grade of each object on the basis of pre-determined data.

According to one embodiment of the present invention, referring to FIG. 1, it is a schematic diagram illustrating an exemplary arrangement of non-limiting elements of a grading machine which is installed with a novel color based optical grading system of the present invention which works with a conveyor which is a transparent surface carrying objects to be graded according to one embodiment of the present invention. The optical grading system is based on external characteristics like size, shape, surface characteristics including color, defects, water marks, oil marks, or any other characteristics. According to one embodiment of the present invention, referring to FIG. 1 is a schematic diagram illustrating an exemplary arrangement of non-limiting elements of a grading machine which is installed with a novel color based optical grading system of the present invention which works with a conveyor which is a transparent surface for carrying objects to be graded. The exemplary grading machine comprising of non-limiting elements: a main frame (301) for arranging all elements of the grading machine on or around the main frame; a hopper (303); a feeding unit (305) to singulate objects; at least one a flat transparent conveyor (309) which is an assembly of multiple flat transparent surfaces forming multiple trays; two boxes (311a) and (311b) are shown below and above the conveyor (309) respectively; an embedded intelligence unit comprises of master controller (315); an ejection unit (317) for ejection of different grades which are pre-determined by master controller; and multiple collecting locations (319) for collecting multiple grades. There is requirement of multiple advanced optics units due to presence of multiple channels in the grading machine for detailed analysis of each object with multi-reflectance and multi-angle views. There can be multiple tray assemblies which are placed parallel to each other to make a transparent conveyor (309). These two boxes (311a and 311b) comprising multiple advanced optics units along with master controller (315) constitute the novel color based optical grading system with multi-reflectance and multi-angle views for grading objects. The novel color based optical grading system comprises of: multiple advanced optics units and at least one master controller. Each advanced optics unit is co-related with all advanced optics units of the novel color based optical grading system so as to grade multiple grades in single pass with multi-reflectance and multi-angle views for grading objects. Each box comprises of multiple advanced optics units (T1, T2 . . . Tn) and each optics unit (T1 or T2 or . . . Tn) comprises of multiple programmable cameras, multiple spectral light sources, multiple adjustable mirrors/prisms, a mirror/prism adjustment assembly to ensure the enhanced surface analysis of the objects; at least one backlighting domes (D1 or D2, or Dn) are used to provide uniform backlight for capturing objects in multi-reflection and multi-angle views and at least one image processing unit for processing images of each objects.

When objects are fed into the hopper (303), there is requirement of a specialized feeding unit (305) which is coupled with multiple feed sensors and at least one feed controller to feed objects singularly and accurately at pre-defined positions on multiple flat transparent surfaces of conveyor (309) in such a way that every flat transparent surface carries one object at a time, wherein multiple flat transparent surfaces themselves make the conveyor (309) which is in motion. Each flat transparent surface of the conveyor (309) provides the facility for multi-vision of a single given object by multiple programmable cameras and multiple mirrors to identify the type or grade of the objects.

The grading machine has multiple channels, wherein in each channel of the machine comprises of multiple flat transparent surfaces, each object on each flat transparent surface of the tray is exposed to multiple programmable cameras using multiple mirrors, for multi-reflection and multi-angle view based analysis of each object. To ensure the non-obvious regions or sides of the irregular or uneven objects which are not visible directly to the multiple programmable cameras will become visible by using multiple mirrors and/or prisms of the advanced optics unit which redirects the light reflecting from objects to the multiple programmable cameras which enables them to capture multi-reflection and multi-angle based views to analyze each object. Opposite of each optics unit, a separate backlighting dome is provided which comprises of multi-colored, flashing, non-flashing back lights covered with a diffusion sheet. The backlighting domes are used to provide the uniform and proper backlight for multi-reflectance and multi-angle based view capturing of object. The diffusion sheet is provided optionally with the backlighting dome to avoid the direct view/capture of backlights in the cameras. The multiple backlighting domes are arranged in such a way that there lays flat transparent surfaces between multiple backlighting domes and multiple optics units. The sideways features may include certain characteristics like sideways lighting from different sides, so that multiple programmable cameras above the conveyor can analyze all the side views and top view of object, likewise multiple programmable cameras below the conveyor can analyze all the side views and bottom view of object to capture multi-reflection and multi-angle based views of the objects for thorough analysis to ultimately grade them into multiple grades in a single pass with higher accuracy and in an efficient manner. The multiple programmable cameras are adjustable so as to get the better views of side features. The images captured by multiple programmable cameras taking multi-reflection and multi-angle based views are processed by respective image processing unit of corresponding advanced optics unit. The master controller (315) receives the signals from the image processing unit and further decides the final grade of the objects based on pre-determined data. The master controller (315) intelligently remembers the position of the single/individual object dropped on each flat transparent surface of each tray on the conveyor (309) and accordingly sends signals to the ejection unit (317). The ejection unit (317) then ejects each object in respective collecting location (319) according to grade of each object. Likewise, multiple objects are graded into multiple grades in a single pass with increased efficiency in the grades as well. The grading machine comprises of multiple collecting locations (319) so as to collect 'n' number of grades in a single pass (where 'n' is a natural positive integer).

Figure 2:
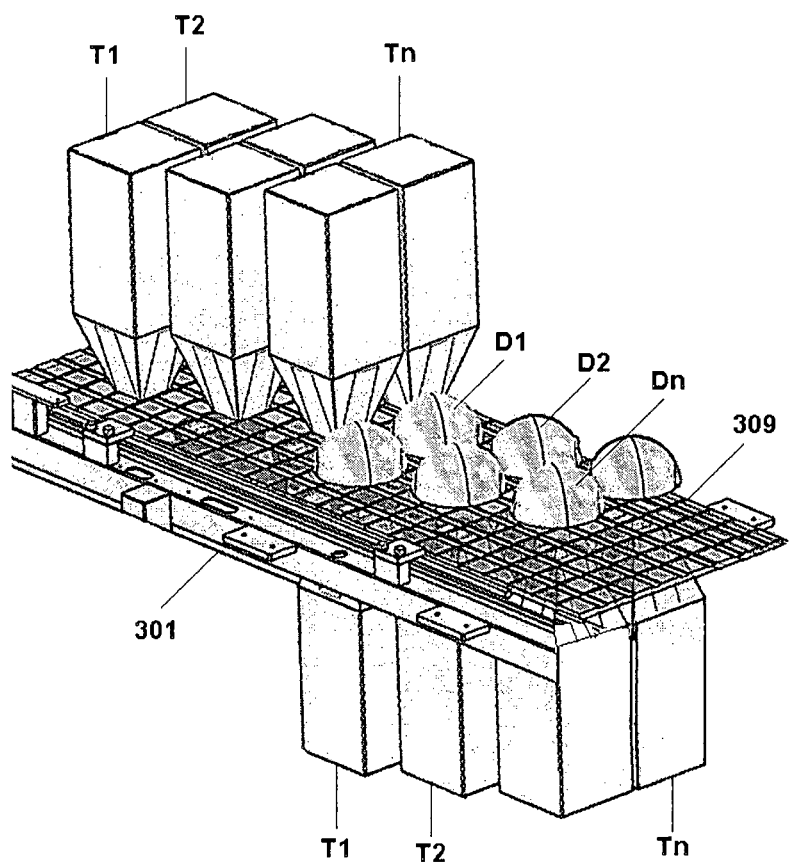
FIG. 2 is an enlarged isometric view of multiple advanced optics units of a novel color based optical grading system showing exemplary arrangement of multiple advanced optics units placed below and above the transparent conveyor according to one embodiment of the present invention.

According to one embodiment of the present invention, referring to FIG. 2 is an enlarged isometric view of multiple advanced optics units of a novel color based optical grading system showing exemplary arrangement of multiple advanced optics units placed below and above the transparent conveyor. FIG. 2 illustrates arrangement of multiple advanced optics units placed below and above the transparent conveyor. Accordingly, multiple optics units (T1, T2 . . . Tn) placed below and above the conveyor (309) which can be arranged on (301) main frame. The number of advanced optics units arranged below the conveyor (309) and above the conveyor (309) are shown as T1, T2 . . . Tn. Each single advanced optics unit placed below the conveyor (309) is focused from the bottom side on the single flat transparent surface. Similarly, each single optics unit placed above the conveyor (309) is focused from the top side on the single flat transparent surface. Conveyor (309) comprises of multiple trays and each tray may comprise of 'n' (here 'n' denotes a natural positive integer) number of flat transparent surfaces. So, the arrangement of multiple advanced optics units (T1, T2 . . . Tn) below and above the conveyor (309) is such that there should be exactly two optics units for covering both top and bottom sides of flat transparent surfaces of each channel covering it from both the sides i.e. top and bottom sides of the conveyor. The aim of using two optics units for covering both top and bottom sides of flat transparent surfaces of each channel is to get all the color details of object such as damage, discolor etc. Multiple backlighting domes (D1, D2, . . . Dn) are provided respectively opposite of multiple optics units to provide uniform backlight for capturing objects in multi-reflection and multi-angle based views. Each backlighting dome comprises of multi-colored, flashing, non-flashing back lights covered optionally with a diffusion sheet. The diffusion sheet is such that the color of the sheet will change as per the change in backlight color for different objects. The backlighting domes are used to provide the uniform and proper backlight for multi-reflectance and multi-angle based view capturing of objects. The diffusion sheet is provided optionally with the backlighting dome to avoid the direct view/capture of backlights in the cameras. The position of the backlighting dome is such that there lays a flat transparent surface between each backlighting dome and each advanced optics unit. So, there are multiple back lighting backlighting domes for multiple advanced optics units. As the flat transparent surfaces in each tray may be 'n' (here 'n' denotes a natural positive integer) in number, the number of advanced optics units may also be 'n' (here 'n' denotes a natural positive integer). The arrangement of multiple advanced optics units below and above the conveyor (309) may be changed such that there should be exactly two advanced optics units for covering both top and bottom sides of flat transparent surfaces of each channel covering it from both the sides i.e. top and bottom sides of the conveyor (309). The cameras must be placed at a specific distance from the flat transparent surface and a resolution to get a proper focus of multiple mirror reflections & flat transparent surface.

Figure 3:
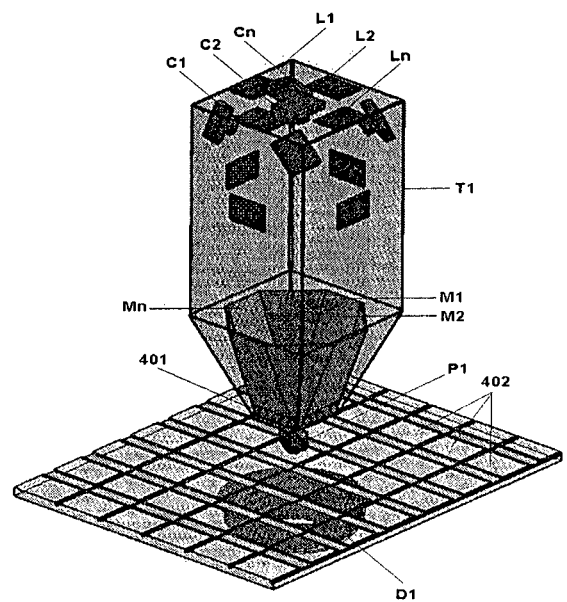
FIG. 3 is an enlarged isometric view of a single advanced optics unit which is placed above the transparent conveyor and is illustrating all constituting elements of a single advanced optics unit along with constituting elements of a transparent conveyor according to one embodiment of the present invention.

According to one embodiment of the present invention, referring to FIG. 3 is an enlarged isometric view of a single advanced optics unit which is placed above the transparent conveyor and is illustrating all constituting elements of a single advanced optics unit. The single advanced optics unit T1 comprises of multiple programmable cameras (C1, C2, ... Cn), multiple spectral light sources (L1, L2, ... Ln), multiple mirrors/prisms (M1, M2, ... Mn), mirror adjustment assembly (401), a backlighting dome (D1) and an advanced image processing unit (not shown in FIG. 3). The multiple programmable cameras (C1, C2, ... Cn) used here can be "synchronous", "asynchronous", "regular", "color" or "multi-spectral" cameras. The object (P1) is shown as an object of interest. One flat transparent surface out of multiple flat transparent surfaces (402) is shown below the advanced optics unit which provides the facility for multi-vision of a single given object (P1) by multiple programmable cameras (C1, C2, ... Cn). For multi-reflectance and multi-angle view based capturing of object (P1) the backlighting dome (D1) is provided respectively opposite to advanced optics unit (T1) to provide uniform backlight for capturing object (P1) in multi-reflection and multi-angle based views. Backlighting dome (D1) comprises of multi-colored, flashing, non-flashing back lights' covered with a diffusion sheet, and the presence of diffusion sheet is absolutely optional for the purposes of this invention. The diffusion sheet can be made up of any plastic material, and the diffusion sheet material can be changed as per the application. The diffusion sheet is such that the color of the sheet will change as per the change in backlight color for different objects. The backlighting dome (D1) is used to give the uniform and proper backlight for multi-reflectance and multi-angle based view capturing of object (P1). The diffusion sheet is provided with the backlighting dome to avoid the direct view/capture of backlights in the cameras. The multiple programmable cameras (C1, C2, ... Cn) work at different frequencies of electromagnetic spectrum like visible, ultra-violet, infra-red etc. The multiple light sources (L1, L2, ... Ln) used are also multi-spectral for efficient approach for recovering spectral reflectance from an object. These multiple spectral light sources (L1, L2, ... Ln) are having different spectra to illuminate the object of interest (P1). The multiple spectral light sources (L1, L2, ... Ln) can be flash lighting, continuous lighting and some of them can be triggered with some respective cameras while others can be turned off. The multiple mirrors/prisms (M1, M2, ... Mn) are used to get multi-reflectance and multi-angle based views of objects conveying on multiple flat transparent surfaces (402). The mirror adjustment assembly (401) is used to adjust the angles of the mirrors (M1, M2, ... Mn) relative to the object (P1) and also used for varying vertical or horizontal distance of mirrors (M1, M2, ... Mn) from the flat transparent surface so that the multi-reflectance and multi-angled views can be captured properly by the camera using multiple mirrors (M1, M2, ... Mn). The mirrors (M1, M2, ... Mn) have to be separated from one another which can be done by either centroid values of objects or by applying a thin tape as an indicator to make out difference. The arrangement of multiple programmable cameras (C1, C2, ... Cn), multiple spectral light sources (L1, L2, ... Ln), multiple mirrors/prisms (M1, M2, ... Mn) and backlighting dome (D1) can be changed according to the object being graded, so that the cameras (C1, C2, ... Cn) can get multi-reflectance and multi-angle based views of the object properly using multiple mirrors/prisms (M1, M2, ... Mn) and multiple spectral light sources (L1, L2, ... Ln).

There is a co-ordination between the multiple programmable cameras (C1, C2, ... Cn), the multiple spectral light sources (L1, L2, ... Ln), multiple mirrors/prisms (M1, M2, ... Mn) and multi-colored backlights placed inside the backlighting dome (D1), for accurate analysis of each object using multi-reflection and multi-angle based view of each object. Each programmable camera (spectral camera) knows the exact position and orientation of each mirror. Multispectral light sources are correlated with all the cameras and the multi-spectral light sources ((L1, L2, ... Ln) can be flash lighting, continuous lighting and some of them can be triggered with some respective cameras while others can be turned off as per the application. Multiple spectral light sources (L1, L2, ... Ln) can focus on single mirror/prism or single spectral light source can focus on multiple mirrors/prisms (M1, M2, ... Mn) using single or multiple programmable cameras (multi-spectral). The casing of the cameras (C1, C2, ... Cn) can be designed with focused multiple spectral light sources (L1, L2, ... Ln) along the lens cover for better illumination of the object from the mirrors/prisms (M1, M2, ... Mn). As the conveying object (P1) comes above the advanced optics unit (T1) placed below the conveyor, camera (C1) placed at the bottom surface of the advanced optics unit (T1) captures the bottom view of the object. Other cameras (C2, C3 ... Cn) will capture the side views of the object using the redirected light reflecting from mirrors/prisms (M1, M2, ... Mn). Here the respective backlighting dome (D1) placed opposite to advanced optics unit (T1) will provide the required uniform color backlights according to the type of object. These different images are processed by the image processing unit of that particular advanced optics unit (T1). Further, the image processing unit signals the master controller about the grade of particular object. The master controller intelligently remembers the position of each object on an individual flat transparent surface of the conveyor. As the object moves further, the object comes below the advanced optics unit (T1) placed above the conveyor. Camera (C1) placed on top surface of the advanced optics unit (T1) captures the top view of the object. Other cameras (C2, C3 ... Cn) will capture the side views of the object using the redirected light reflecting from mirrors/prisms (M1, M2, ... Mn). Here the respective backlighting dome (D1) placed opposite to advanced optics unit (T1) will provide the required uniform color backlighting according to the type of object. These different images are processed by the image processing unit of that particular advanced optics unit T1. Further, the image processing unit signals the master controller about the grade of particular object. Based on the position of the object on the flat transparent surface, the cameras (C1, C2, . . . Cn) will decide the compensation factor which will calculate the possible shrinkage or expansion of object in the respective mirrors (M1, M2, . . . Mn) to get the exact size images of object. The master controller has the database/look-up tables comprising (x, y) co-ordinates of object placed on any position on the flat transparent surface which is the pre-determined data. Master controller compares the grade of object and according to the priority of the property of the object to be graded the master controller decides the final grade of object. Due to this unique co-ordination between the different elements of the advanced optics unit, the multiple programmable cameras (C1, C2, . . . Cn) are able to capture the multi-side and enhanced views of each object which enables the image processing unit of multiple programmable cameras (C1, C2, . . . Cn) of corresponding advanced optics unit to decide the exact grade of each object according to its enhanced properties.

Figure 4:
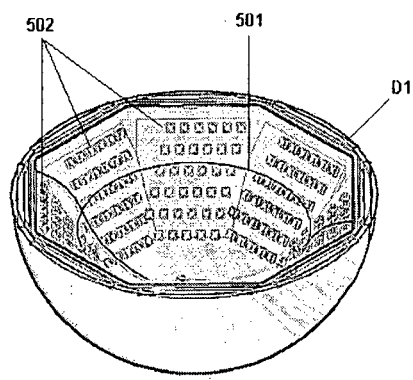
FIG. 4 is an enlarged isometric view of a single backlighting dome illustrating multi-colored backlighting and a diffusion sheet as its constituting elements according to one embodiment of the present invention.

According to one embodiment of the present invention, referring to FIG. 4, it is an enlarged isometric view of a single backlighting dome illustrating multi-colored backlighting and a diffusion sheet as its constituting elements. FIG. 4 shows a backlighting dome (D1) comprises of multi-colored backlighting (502) and a diffusion sheet (501). Backlighting comprises of multi-colored, flashing, non-flashing back lights (502) covered with a diffusion sheet (501). The diffusion sheet (501) is such that the color of the sheet will change as per the change in backlight color requirement for the different objects. The backlighting dome (D1) is used to give the uniform and proper backlight for multi-reflectance and multi-angle based view capturing of object (P1). The diffusion sheet is provided with the backlighting dome (D1) to avoid the direct view/capture of backlights in the cameras. The position of the backlighting dome (D1) is such that there lays a flat transparent surface between each backlighting dome and each advanced optics unit.

EXAMPLES

Few working examples are described herein below which exhibits the commercial importance of proposed novel color based optical grading system with multi-reflectance and multi-angle views for grading objects of different external characteristics:

1. The defects in the stomach area of cashews are not visible by existing color grading systems/machines due to lack of side view analysis. The proposed novel color based optical grading system uses multi-reflection and multi-angle based views to analyze cashews using multiple mirrors and multiple programmable cameras for accurate grading of cashew nuts which is not possible accurately with existing color grading machines.
2. In the bulk processing of raisins due to its soft surface, the small sticks connected to it may get inside it. So, while grading due to inefficient side view analysis, sticks inside raisins do not get detected. The proposed novel color based optical grading system correlates between all the data collected using multi-reflection and multi-angle view analysis of raisins to make a decision about accurate grade of each raisin since raising shows significant range of color shades variation.
3. While grading the areca-nut, the differentiation between the different smaller white portions is analyzed by the multiple programmable cameras which capture multi-reflection and multi-angle based views of each areca nut.
4. The novel color based optical grading system grades the multi-colored precious and semiprecious stones in a single pass accurately using thorough side view analysis.

Figure 5:
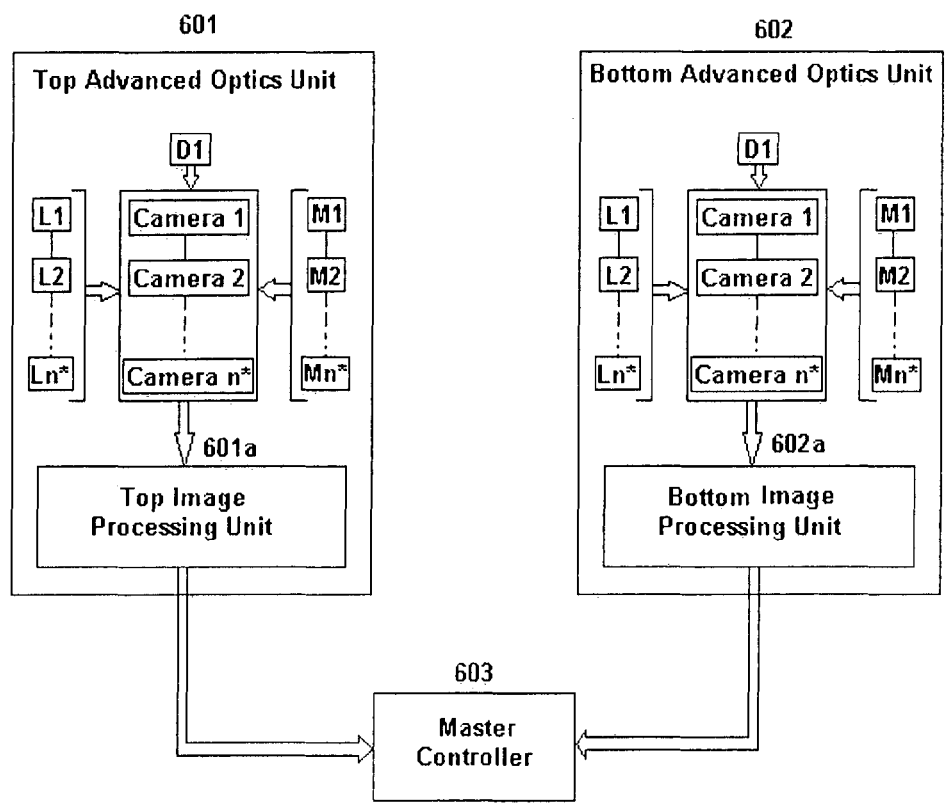
FIG. 5 is a flow diagram illustrating different non-limiting steps involved in a novel color based optical grading method for grading objects according to another embodiment of the present invention.

According to another embodiment of the present invention, referring to FIG. 5, it is a flow diagram illustrating different non-limiting steps involved in a novel color based optical grading method for grading objects. Objects of different external characteristics are subjected for optical grading, wherein objects are singularized before subjecting for optical grading in optical grading system so that objects are placed into the multiple flat transparent surfaces of trays having multi-vision facility in a position of a single object on a single flat transparent surface, wherein multiple flat transparent surfaces themselves make the conveyor which is in motion, wherein the transparent surface can be flat or bordered cups or of any other shape of transparent surface, wherein the objects are placed singularly at pre-defined positions on multiple flat transparent surfaces of conveyor in such a way that every flat transparent surface carries one object at a time.

FIG. 5 shows the entire method of analysis of a single object. The novel color based optical grading method. Once the objects are placed into the multiple flat transparent surfaces of trays having multi-vision facility, wherein each channel is having at least one top advanced optics unit (601) and at least one bottom optics advanced unit (602). Each object of each channel of the grading machine is viewed by one top advanced optics unit (601) and at least one bottom advanced optics unit (602). As the method grades multiple objects in a single pass, there are multiple channels in which objects are subjected for optical grading. There are multiple advanced optics units.

As shown in FIG. 5, Top advanced optics unit (601) comprises of multiple programmable cameras shown as camera 1, camera 2 . . . which may extend till camera n* (where n* is a natural positive integer), multiple spectral light sources shown as L1, L2, . . . which may extend till Ln* (where n* is a natural positive integer), multiple adjustable mirrors/prisms shown as as M1, M2, . . . which may extend till Mn* (where n* is a natural positive integer), image processing unit, at least one backlighting dome shown as D1, a mirror adjustment assembly (Not shown in FIG. 5), and top image processing unit shown as 601a. At least one backlighting dome is present in the advanced optics unit to ensure the enhanced surface analysis of the object by providing uniform backlight for capturing objects in multi-reflection and multi-angle views. Bottom advanced optics unit (602) comprises of multiple programmable cameras shown as camera 1, camera 2 . . . which may extend till camera n* (where n* is a natural positive integer), multiple spectral light sources shown as L1, L2, . . . which may extend till Ln* (where n* is a natural positive integer), multiple adjustable mirrors/prisms shown as as M1, M2, . . . which may extend till Mn* (where n* is a natural positive integer), image processing unit comprises of at least one image processing unit, at least one backlighting dome shown as D1, a mirror adjustment assembly (Not shown in FIG. 5), and bottom image processing unit shown as 602a.

At least one backlighting dome is present in the advanced optics unit to ensure the enhanced surface analysis of the object are used to provide a uniform backlight for capturing objects in multi-reflection and multi-angle views.

Each single advanced optics unit is placed below the conveyor is focused from the bottom side (602) on the single flat transparent surface. Similarly, each single optics unit placed above the conveyor is focused from the top, side (601) on the single flat transparent surface. So, the arrangement of multiple advanced optics units (T1, T2 . . . Tn) below and above the conveyor is such that there should be exactly two advanced optics units for covering both top and bottom sides of each flat transparent surfaces of each channel covering it from both the sides i.e. top and bottom sides of the conveyor belt. Two advanced optics units (601) and (602) are adapted for covering both top and bottom sides of flat transparent surfaces of each channel so as to get all the color details of every single object along with all other external characteristics. One backlighting dome (D1 or D2) is provided opposite of each single advanced optics units to provide uniform backlight for capturing objects in multi-reflection and multi-angle based views. Each backlighting dome (D1 or D2) comprises of multi-colored, flashing, non-flashing back lights covered with a diffusion sheet to avoid the direct view/capture of backlights in the cameras, wherein the color of diffusion sheet can be changed as per the change in backlight color for different objects and this backlighting dome is used to provide the uniform and proper backlight for multi-reflectance and multi-angle based view capturing of objects. The backlighting dome is positioned in such a manner that there lays a single flat transparent surface (with single object) between each backlighting dome and each advanced optics unit. So there is single back lighting dome for each advanced optics unit.

In FIG. 5, disclosed is the entire flow of capturing of images and processing of said images and deciding grade of a given object, considering only single object in single transparent surface. When a single conveying object comes above bottom advanced optics unit (602) placed below said conveyor, bottom camera placed at the bottom surface of the bottom advanced optics unit (602) captures the bottom view of the object, other cameras capture the side views of same object using the redirected light reflecting from said mirrors/prisms, and respective backlighting dome placed opposite to bottom advanced optics unit (602) provides the required uniform color backlighting according to the type of object, wherein the real object image obtained from bottom camera (602) and reflected object image obtained by other cameras are processed by bottom image processing unit (602a) of corresponding advanced optics unit (602) and signals to the master controller (603) about the grade of particular object, wherein the master controller (603) remembers the position of corresponding object on an individual flat transparent surface of the conveyor, further when same object moves further to reach below said top advanced optics unit (601) placed above said conveyor, and top camera placed on top surface of top advanced optics unit (601) captures the top view of said object, whereas other cameras capture the side views of said object using the redirected light reflecting from mirrors/prisms, whereas the respective backlighting dome placed opposite to said advanced optics unit provides the required uniform color backlighting according to the type of object, and wherein the real object image obtained from top camera and reflected object image obtained by other cameras are processed by top image processing unit of corresponding advanced optics unit and signals to said master controller (603) about the grade of particular object, further based on the position of said object on the flat transparent surface, all cameras (C1, C2, . . . Cn) decides the exact size images of said object and said master controller compares each grade based on pre-determined data and according to the priority of the property of said object to be graded said master controller decides the final grade of object. The novel color based optical grading method for grading objects provides multiple grades in a single pass due to multiple channeled nature of the method.

EXAMPLE

The novel color based optical grading method for grading objects of different external characteristics is carried out by using multiple programmable cameras with the image processing unit of advanced optics unit to enhance sideways features of each object, so that any defect or husk (ex. cashew husk) attached to the object can be determined very efficiently, rapidly and easily.

Other embodiments of the invention will be apparent to those skilled in the art from consideration of the specification and practice of the invention disclosed herein. It is intended that the described aforementioned embodiments of the invention to be considered as exemplary only and not restrictive in any sense, with the true scope and spirit of the invention.

What is claimed is:

1. A novel color based optical grading system with multi-reflectance and multi-angle views for grading objects of different external characteristics, said optical grading system comprising of multiple advanced optics units which are placed above and below a flat transparent conveyor which is an arrangement of multiple trays forming multiple trays, where each tray is an assembly of multiple flat transparent surfaces with facility for multi-vision of single object in a single flat transparent surface in a pre-defined position; and at least one master controller; wherein the arrangement of said multiple advanced optics units above and below the conveyor is always kept in a way so as to provide exactly two advanced optics units for covering both top and bottom sides of each object to be graded; and wherein each advanced optics unit comprises of:

multiple programmable cameras which are placed at a specific distance from said flat transparent surface and said multiple cameras are adapted to capture different views of each object at different frequencies of electromagnetic spectrum and to get a proper focus of said flat transparent surface;

multiple mirrors/multiple prisms to get redirected light reflected from side views of each object to said cameras which enable said multiple cameras to capture multi-reflectance and multi-angle based views of said object to analyze said object and said multiple mirrors/prisms also enables said cameras to get a proper focus of reflections of said multiple mirrors/prisms and said object;

at least one mirror/prism adjustment assembly to adjust the angles of said multiple mirrors or multiple prisms relative to the position of said object on said flat transparent surface; to adjust said mirrors/prisms according to size variations of multiple objects; and to vary vertical or horizontal distance of said mirrors/prisms from said flat transparent surface;

multiple spectral light sources to illuminate every side view of said object at different frequencies of electromagnetic spectrum, wherein said spectral light sources are correlated with all said cameras and said light sources is either flash lighting or continuous lighting, and some of said light sources are triggered with some respective cameras while others light sources are turned off as per the requirement;

at least one backlighting dome placed exactly opposite of each advanced optics unit, wherein said each backlighting dome is arranged in said optical grading system in such a way that there lays at least one flat transparent surface between each said backlighting dome and each advanced optics units to provide uniform backlight for capturing objects in multi-reflection and multi-angle based views and said backlighting dome comprises of multi-colored, flashing or non-flashing back lights, wherein said backlighting dome is optionally covered with a diffusion sheet which is adapted to change in color of said sheet according to different characteristics of said object; and at least one image processing unit for processing multi-reflectance and multi-angle based views of said object taken by said cameras; wherein said multiple cameras said multiple spectral light sources, said multiple adjustable mirrors/multiple adjustable prisms, said mirror adjustment assembly, said backlighting dome and said image processing unit work collaboratively to ensure the enhanced surface analysis of said object, and further wherein said advanced optics unit enhances the sideways features of said objects including sideways lighting from different sides using multiple reflections from multiple angles by enabling said multiple cameras to analyze said object from all side views and also from top and bottom views for accurate complete analysis of said object; wherein said master controller of said optical grading system intelligently remembers the position of each said object dropped on each flat transparent surface of each tray and decide the final grade of each said object based on inputs received from each image processing unit of corresponding each advanced optics unit by comparing said inputs with pre-determined data.

2. The novel color based optical grading system of claim 1, wherein there is a correlation between the said cameras which correlate between all the data collected using multi-reflection and multi-angle based view analysis of each said object and wherein; each said camera knows the exact orientation and position of each mirror/prism to correlate between the images taken by mirror/prism by redirecting light reflected from the side views of said object; each said spectral light source is correlated with all the cameras and can be flash lighting, continuous lighting and some of them can be triggered with some respective cameras while others can be turned off as per the application; a single spectral light source focus on said multiple mirrors/prisms or said multiple spectral light sources focus on single mirror as per the requirement.

3. The novel color based optical grading system of claim 1, wherein each advanced optics unit is co-related with all advanced optics units of the novel color based optical grading system so as to grade objects into multiple grades in single pass with multi-reflectance and multi-angle views for grading multiple objects.

4. The novel color based optical grading system of claim 1, wherein said system identify the type or color grade of individual object with multiple advanced optics unit due to collaborative functioning of said cameras, multiple spectral light sources, multiple adjustable mirrors/prisms, and said backlighting dome due to multi-reflection and multi-angle based views of each object for accurate grading, wherein each said camera knows the exact orientation and position of each mirror/prism to correlate between the images taken by mirror/prism by redirecting light reflected from the side views of said object.

5. The novel color based optical grading system of claim 1, wherein multiple mirrors and multiple prisms of each said advanced optics unit are adjustable to obtain enhanced views of side features taking said multi-reflection and multi-angle based views which are processed by corresponding image processing unit of corresponding advanced optics unit and sends signal to said master controller to decide the final grade of said object based on pre-determined data.

6. A novel color based optical grading method for grading objects based on different external characteristics, wherein said method comprising the steps of:

Subjecting objects of different external characteristics for optical grading, wherein objects are singularized before subjecting for optical grading in optical grading system so that objects are placed into multiple flat transparent surfaces themselves which make a conveyor which is in motion, said multiple flat transparent surfaces of trays have multi-vision facility, and objects are placed singularly at pre-defined positions on multiple flat surfaces of conveyor in such a way that every flat transparent surface carries one object at a time;

conveying of each said object in said flat transparent surface of said conveyor where at least one advanced optics units for analyzing each object is placed below said conveyor and one advanced optics unit is placed above said conveyor to analyze each said object;

analyzing single object in single transparent cup by at least two advanced optics units in wherein said analysis is carried out collaboratively by said two advanced optics unit and a master controller, wherein each advanced optics unit comprises of multiple programmable cameras, multiple mirrors/multiple prisms, at least one mirror/prism adjustment assembly, multiple spectral light sources, at least one backlighting dome optionally covered with a diffusion sheet and at least one image processing unit, wherein out of said two advanced optics unit, one said advanced optics unit is placed below said conveyor, bottom camera placed at the bottom surface of said advanced optics unit captures the bottom view of said object, other cameras capture the side views of same object using the redirected light reflecting from said mirrors/prisms, and respective backlighting dome placed opposite to said advanced optics unit provides the required uniform color backlighting according to the type of object, wherein the real object image obtained from bottom camera and reflected object image obtained by other cameras are processed by corresponding image processing unit of corresponding advanced optics unit and signals to said master controller about the grade of particular object, wherein said master controller remembers the position of corresponding object on an individual flat transparent surface of the conveyor, further when same said object moves further to reach below said same advanced optics unit placed above said conveyor, and top camera placed on top surface of said same advanced optics unit captures the top view of said object, whereas other cameras capture the side views of said object using the redirected light reflecting from multiple mirrors/prisms, whereas the respective backlighting dome placed opposite said advanced optics unit provides the required uniform color backlighting according to the type of object, and wherein the real object image obtained from top camera and reflected object image obtained by other cameras are processed by corresponding image processing unit of corresponding advanced optics unit and signals to said master controller about the grade of particular object, further based on the position of said object on the flat transparent surface, all said cameras decides the exact size images of said object and said master controller compares said bottom view and said top view images of said object based on pre-determined data and according to the priority of color variation or color defects or other external characteristics on both sides of said object, said master controller decides the final grade of said object.

7. The novel color based optical grading method of claim 6, wherein due to co-ordination among said cameras, said multiple spectral light sources, said multiple mirrors/prisms and said multi-colored backlights of said backlighting dome, said cameras analyzes accurately each object to know the exact grade of said object.

8. The novel color based optical grading method of claim 6, wherein said multiple spectral light sources are provided to focus on single mirror/prism or single spectral light source is provided to focus on multiple mirrors/prisms in combination with single or multiple said cameras.

9. The novel color based optical grading method of claim 6, wherein a single back lighting dome is placed for each advanced optics unit, and said backlighting dome is placed such that there lays a flat transparent surface between each backlighting dome and each optics unit, and wherein said backlighting dome comprises of multi-colored, flashing, non-flashing back lights and said backlighting dome is optionally covered with a diffusion sheet, and said backlighting dome provides the uniform and proper backlight for multi-reflectance and multi-angle based view capturing of object, and said diffusion sheet is provided to distribute multi-coloured light sources uniformly to said backlighting dome to avoid the direct View/capture of backlights in said cameras, wherein the color of said diffusion sheet changes as per the change in backlight color for different objects.

10. The novel color based optical grading method of claim 6, wherein said method grades multiple objects in multiple grades in a single pass due to multiple channeled operation of said method.

* * * * *